US011026918B2

(12) United States Patent
Harijith et al.

(10) Patent No.: US 11,026,918 B2
(45) Date of Patent: Jun. 8, 2021

(54) METHOD OF PREVENTING OR TREATING A PULMONARY DISEASE OR CONDITION

(71) Applicant: THE BOARD OF TRUSTEES OF THE UNIVERSITY OF ILLINOIS, Urbana, IL (US)

(72) Inventors: Anantha Harijith, Naperville, IL (US); Viswanathan Natarajan, Frankfort, IL (US); Roberto F. Machado, Hinsdale, IL (US); Jeffrey Jacobson, Oak Park, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 330 days.

(21) Appl. No.: 15/527,103

(22) PCT Filed: Nov. 24, 2015

(86) PCT No.: PCT/US2015/062332
§ 371 (c)(1),
(2) Date: May 16, 2017

(87) PCT Pub. No.: WO2016/085933
PCT Pub. Date: Jun. 2, 2016

(65) Prior Publication Data
US 2017/0360749 A1    Dec. 21, 2017

Related U.S. Application Data

(60) Provisional application No. 62/083,693, filed on Nov. 24, 2014.

(51) Int. Cl.
*A61K 31/40* (2006.01)
*A61K 9/00* (2006.01)
*A61M 15/00* (2006.01)
*A61K 31/402* (2006.01)

(52) U.S. Cl.
CPC .............. *A61K 31/40* (2013.01); *A61K 9/008* (2013.01); *A61K 31/402* (2013.01); *A61M 15/009* (2013.01)

(58) Field of Classification Search
CPC .......... A61K 31/40; A61K 9/00; A61M 15/00
See application file for complete search history.

(56) References Cited

U.S. PATENT DOCUMENTS

| | | | | |
|---|---|---|---|---|
| 8,372,888 B2 | 2/2013 | Zipkin et al. | | 514/653 |
| 8,436,186 B2 | 5/2013 | Stieber et al. | | 546/205 |
| 8,557,800 B2 | 10/2013 | Smith et al. | | 514/195 |
| 2006/0270630 A1 | 11/2006 | Smith et al. | | 514/78 |
| 2007/0020190 A1 | 1/2007 | Razzetti et al. | | 424/45 |
| 2007/0032531 A1 | 2/2007 | Smith et al. | | 514/342 |
| 2012/0214858 A1 | 8/2012 | Lynch et al. | | 514/423 |
| 2012/0252815 A1 | 10/2012 | Stieber et al. | | 514/236.8 |
| 2014/0187607 A1 | 7/2014 | Russell et al. | | 514/44 A |

FOREIGN PATENT DOCUMENTS

| WO | WO 2009/156041 | 12/2009 |
|---|---|---|
| WO | WO 2010/078247 | 7/2010 |
| WO | 2013011946 | 1/2013 |
| WO | 2014118556 | 8/2014 |
| WO | 2014157382 | 10/2014 |

OTHER PUBLICATIONS

Baek, et al. "Synthesis of selective inhibitors of sphingosine kinase 1" (2013) *Chem. Commun.* 49:2136-2138.
Byun, et al. "Novel sphingosine-containing analogues selectively inhibit sphingosine kinase (SK) isozymes, induce SK1 proteasomal degradation and reduce DNA synthesis in human pulmonary arterial smooth muscle cells" (2013) *Med. Chem. Commun.* 4:1394.
Chen, et al. "The sphingosine kinase 1/sphingosine-1-phosphate pathway in pulmonary arterial hypertension" (2014) *Am. J. Resp. Crit. Care Med.* 190:1032-43.
DeJonghe, et al. "Structure-activity relationship of short-chain sphingoid bases as inhibitors of sphingosine kinase" (1999) *Bioorg. Med. Chem. Lett.* 9:3175-3180.
Edsall, et al. "N,N-Dimethylsphingosine is a potent competitive inhibitor of sphingosine kinase but not of protein kinase C: modulation of cellular levels of sphingosine 1-phosphate and ceramide" (1998) *Biochemistry* 37:12892-8.
Gorshkova, et al. "Inhibition of serine palmitoyltransferase delays the onset of radiation-induced pulmonary fibrosis through the negative regulation of sphingosine kinase-1 expression" (2012) *J. Lipid Res.* 53:1553-68.
Gustin, et al. "Structure guided design of a series of sphingosine kinase (SphK) inhibitors" (2013) *Bioorg. Med. Chem. Lett.* 23:4608-4616.
Harijith, et al. "Sphingosine kinase 1 deficiency confers protection against hyperoxia-induced bronchopulmonary dysplasia in a murine model: role of S1P signaling and Nox proteins" (2013) *Am. J. Pathol.* 183:1169-82.
Huang, et al. "Targeting sphingosine kinase 1 attenuates bleomycin-induced pulmonary fibrosis" (2013) *FASEB J.* 27:1749-1760.
Huang & Natarajan "Sphingolipids in pulmonary fibrosis" (2015) *Adv. Biol. Regul.* 57:55-63.
Huang, et al. "Sphingosine-1-phosphate lyase is an endogenous suppressor of pulmonary fibrosis: Role of S1P signalling and autophagy" (2015) *Thorax* doi:10.1136/thoraxjnl-2014-206684.
Johnson, et al. "Intrinsic cytotoxicity and chemomodulatory actions of novel phenethylisothiocyanate sphingoid base derivatives in HL-60 human promyelocytic leukemia cells" (2004) *J. Pharmacol. Exp. Ther.* 309:452-461.
Kennedy, et al. "Structure guided design of a series of sphingosine kinase(SphK) inhibitors" (2011) *J. Med. Chem.* 54:3524-48.

(Continued)

*Primary Examiner* — Zohreh A Fay
(74) *Attorney, Agent, or Firm* — Licata & Tyrrell P.C.

(57) ABSTRACT

A pharmaceutical composition for aerosol administration and method of preventing or treating a pulmonary disease or condition in a subject with a SphK1 inhibitor are provided.

**8 Claims, 7 Draw

(56) References Cited

OTHER PUBLICATIONS

Niro, et al. "(3Z)-2-Acetylamino-3-octadecen-1-ol as a potent apoptotic agent against HL-60 cells" (2004) *Bioorg. Med. Chem.* 12:45-51.
Schnute, et al. "Modulation of cellular S1P levels with a novel, potent and specific inhibitor of sphingosine kinase-1" (2012) *Biochem. J.* 444:79-88.
International Preliminary Examination Report in PCT/US15/62332 dated May 30, 2017.
International Search Report and Written Opinion in PCT/US15/62332 dated Feb. 5, 2016.
Extended European Search Report dated Jul. 4, 2018 from EP 15862576.4 filed Nov. 24, 2015.
MacRitchie et al. "Effect of the Sphingosine Kinase 1 Selective Inhibitor, PF-543 on Arterial and Cardiac Remodelling in a Hypoxic Model of Pulmonary Arterial Hypertension" Cellular Signalling 2016 28:946-955.
Nishiuma et al. "Inhalation of Sphingosine Kinase Inhibitor Attenuates Airway Inflammation in Asthmatic Mouse Model" American Journal of Physiology-Lung, Cellular and Molecular Physiology 2008 L1085-L1093.

METHOD OF PREVENTING OR TREATING A PULMONARY DISEASE OR CONDITION

INTRODUCTION

This application is the U.S. National Stage Application of PCT/US2015/062332, filed Nov. 24, 2015, which claims the benefit of priority of U.S. Provisional Application No. 62/083,693, filed Nov. 24, 2014, the contents of each of which are incorporated herein by reference in their entireties.

This invention was made with government support under contract numbers P01 HL 098050 and RO1 HL 127342 awarded by the National Institutes of Health. The government has certain rights in the invention.

BACKGROUND

Bronchopulmonary dysplasia (BPD) is a chronic lung disease occurring as a consequence of injury to the rapidly developing premature lungs of a pre-term newborn infant. Preterm babies receive ventilator care and inhaled oxygen supplementation for variable periods of time following delivery and prolonged exposure of preterm lungs to hyperoxia results in inflammation, pulmonary edema, lung injury and ultimately death. BPD is characterized by decreased secondary septation of alveoli resulting in the formation of enlarged simplified alveoli and reduced area for gas exchange. Over 25% of premature infants with birth weights <1500 g develop BPD. Infants with BPD have higher re-hospitalization rates due to asthma, infection, pulmonary hypertension and other respiratory ailments. Many surviving neonatal BPD patients now reaching adulthood show a sharp decline in lung capacity indicating that the adverse effects of insult in the neonatal stage can be long lasting. There is no effective treatment for BPD and strategies to prevent BPD by administering gentler ventilation and other therapeutic approaches have not been effective. Identification of novel signaling pathways linking hyperoxia-induced lung injury in neonatal BPD is necessary for new therapeutic approaches.

A correlation between sphingosine kinase (SphK) activity and lung injury has been, described. For example, increased expression of sphingosine kinase 1 (SphK1) has been found in lung tissues from patients with idiopathic pulmonary fibrosis and bleomycin-treated animals. Further, knockdown of SphK1 or inhibition of SphK activity with a non-selective inhibitor has been shown to reduce intracellular sphinosine-1-phosphate (S1P) generation and TGF-β secretion in a bleomycin-induced lung fibrosis mouse model that was accompanied by reduced phosphorylation of Smad2 and MAPKs in lung tissue (Huang, et al. (2013) *FASEB J.* 27:1749-1760; Huang & Natarajan (2015) *Adv. Biol. Regul.* 57:55-63; Huang, et al. (2015) *Thorax* doi:10.1136/thoraxjnl-2014-206684). Increased lung expression of SphK1 and upregulation of S1P and dihydrosphingosine-1-phosphate (DHS1P) levels has also been demonstrated in a mouse model of radiation-induced pulmonary fibrosis (Gorshkova, et al. (2012) *J. Lipid Res.* 53:1553-68). Similarly, mRNA and protein levels of SphK1, but not SphK2, are significantly increased in the lungs and isolated pulmonary artery smooth muscle cells (PASMCs) from patients with pulmonary arterial hypertension (PAH), and in lungs of experimental rodent models of hypoxia-mediated pulmonary hypertension (HPH) such that SphK1$^{-/-}$ mice and non-selective inhibition of SphK1 provides protection against HPH (Chen, et al. (2014) *Am. J. Resp. Crit. Care Med.* 190:1032-43). Similarly, SphK1 deficiency offers protection against hyperoxia-induced lung injury in mice and non-selective inhibition of SphK1 attenuates hyperoxia-induced S1P generation (Harijith, et al. (2013) *Am. J. Pathol.* 183:1169-82).

Selective inhibitors of SphK1 are described in the art. For example, U.S. Pat. No. 8,557,800 teaches substituted adamantane compounds for inhibiting sphingosine kinase and for treating or preventing inflammatory disease such as asthma or chronic obstructive pulmonary disease, or angiogenic disease such as cancer. Similarly, U.S. Pat. No. 8,372,888 discloses SphK1 inhibitors of use in the treatment of cancer, asthma, anaphylaxis, autophagy, and central nervous system disorders, and U.S. Pat. No. 8,436,186 and US 2012/0214858 describe SphK1 inhibitors of use in the treatment of cancer. US 2012/0252815 describes inhibitors of sphingosine kinase for treating hyperproliferative diseases such as cancer and inflammation-induced diseases such as asthma. WO 2014/118556 further discloses SphK1-selective inhibitors for treating pulmonary arterial hypertension and cancer as well as SphK1 activators for use in diseases such as fibrosis. In addition, WO 2014/157382 describes sphingosine kinase inhibitors for preventing or treating inflammatory bowel disease. Additional sphingosine kinase inhibitors are describy in Edsall, et al. (1998) *Biochemistry* 37:12892-8; DeJonghe, et al. (1999) *Bioorg. Med. Chem. Lett.* 9:3175-3180; Johnson, et al. (2004) *J. Pharmacol. Exp. Ther.* 309:452-461; Niro, et al. (2004) *Bioorg. Med. Chem.* 12:45-51; Baek, et al. (2013) *Chem. Commun.* 49:2136-2138; Gustin, et al. (2013) *Bioorg. Med. Chem. Lett.* 23:4608-4616; Kennedy, et al. (2011) *J. Med. Chem.* 54:3524-48; Byun, et al. (2013) *Med. Chem. Commun.* 4:1394 and Schnute, et al. (2012) *Biochem. J.* 444:79-88.

SUMMARY OF THE INVENTION

This invention provides a method of preventing or treating a pulmonary disease or condition in a subject by administering to a subject in need of treatment an effective amount of a SphK1 inhibitor to prevent or treat the subject's pulmonary disease or condition, wherein the SphK1 inhibitor is cell permeable, has an $IC_{50}$ value of less than 10 μM, has a $K_i$ of less than 10 μM, exhibits at least a 20-fold greater selectivity for SphK1 than SphK2, or a combination thereof. In one embodiment, the pulmonary disease or condition comprises pulmonary hypertension, adult respiratory distress syndrome, restrictive lung disease, chronic obstructive pulmonary disease, bronchiectasis, bronchiolectasis, bronchiolitis, bronchitis, emphysema, a diffuse interstitial or infiltrative lung disease, serofibrinous pleuritis, suppurative pleuritis, hemorrhagic pleuritis, a pleural effusion, idiopathic pulmonary fibrosis, hyperoxia or oxygen-induced lung injury, injury due to drug or chemotherapeutic toxicity, radiation-induced injury, or chemical injury. In another embodiment, the SphK1 inhibitor comprises [(2R)-1-[[4-[[3-(benzenesulfonyl methyl)-5-methylphenoxy]methyl] phenyl]methyl] pyrrolidin-2-yl] methanol (PF-543) or an analog, derivative or pharmaceutically acceptable salt thereof, e.g., a citric acid salt. In certain embodiments, the SphK1 inhibitor is administered to the lungs of the subject.

The invention also provides a method of treating oxygen-induced lung injury in a subject by administering to a subject in need of treatment an effective amount of PF-543, or an analog, derivative or pharmaceutically acceptable salt thereof, to treat the subject's oxygen-induced lung injury.

This invention further provides a pharmaceutical composition for aerosol administration, which includes one or more propellants and PF-543 or an analog, derivative or pharmaceutically acceptable salt thereof. In some embodiments, the pharmaceutical composition is provides in a metered dose inhaler for aerosol administration.

BRIEF DESCRIPTION OF THE DRAWINGS

FIG. 3A, three different doses of PF-543 are administered for 7 days to newborn mice or 3 days to adult mice to optimize the dose. FIG. 3B, nebulized PF-543 is administered 7 days to newborn mice or 3 days to adult mice to demonstrate efficacy of inhaled PF-543 agains hypoxic lung injury. PF-543 dissolved in surfactant is administered to newborn mice on alternate days from PN3 to PN10. FIG. 3C, nebulized PF-543 is administered for 7 days to newborn mice or 3 days to adult mice to demonstrate efficacy of inhaled PF-543 against hyperoxic lung injury.

FIG. 4A, the survival of irradiated control and myriocin-treated groups of C57B1/6 mice. Statistical difference was calculated using a log-rank (Mantel-Cox) test. Animals were treated with 0.375 mg/kg myriocin p.o. 3×/week in 10 g/L glucose in water (pH 3.5). Control animals received only the solvent. FIG. 4B, inhibition of a radiation-induced increase in total SphK activity by myriocin ("Myr," $P_{int}$=0.0478). SphK activity is expressed as pmol S1P formed per minute per mg total cell lysate protein. FIGS. 4C and 4D, Irradiation increases SphK1 mRNA levels (FIG. 4C) and SphK1 protein expression (expressed as SphK1/GAPDH (intensity ratio), FIG. 4D), which are decreased by myriocin (SphK1 protein $P_{int}$=0.0358). FIG. 4E and FIG. 4F, irradiation does not substantially decrease the mRNA levels of SphK2 (FIG. 4E) but significantly decreases its protein expression (expressed as SphK2/GAPDH (intensity ratio), FIG. 4F). Neither parameter is affected by myriocin treatment. *P<0.05, P<0.01, *P<0.001 versus nonirradiated control (n=5). N.S., nonsignificant.

FIGS. 5A-5B, β-actin-normalized quantification of protein demonstrates that SphK1 expression (FIG. 5A), but not SphK2 expression (FIG. 5B), is significantly increased in lungs from patients with PAH when compared with control subjects. Results are expressed as mean±SEM; n=4 per group. *P, 0.05 versus control. FIG. 5C-5D, β-actin-normalized quantification of protein demonstrate that SphK1 expression is significantly increased in mouse lungs (FIG. 5C) and rat lungs (FIG. 5D) after 4-week hypoxia exposure, whereas no changes in SphK2 expression are demonstrated. (n=5 per group). P, 0.01; *P, 0.001 versus normoxia.

FIG. 6A, changes in right ventricular systolic pressure (RVSP). FIG. 6B, changes in RV/(LV+S). FIG. 6C, changes in ratios of wall area to total vessel area of pulmonary arteries less than 50 mm or 50-100 mm in diameter in the lung sections of control and SKI-II-treated groups after normoxia or hypoxia exposure. Results are expressed as mean±SEM; n=6 per group. *P, 0.05; **P, 0.01 versus normoxia without SKI2 group.

FIGS. 7A-7B, β-actin-normalized quantification of western blots probed with anti-SphK1 (FIG. 7A) or anti-SphK2 (FIG. 7B) antibodies. FIG. 7C, Deficiency of SphK1 protects alveolarization of murine neonatal lungs under hyperoxia. Wild-type (C57BL/6J) or Sphk1$^{-/-}$ newborn mice, along with the lactating dams, were exposed to normoxia (NO; open bars) or hyperoxia (HO; filled bars; 75% $O_2$) from PN day 1 for 7 days. On completion of exposure, newborn mice were euthanized, and lungs were removed, embedded in paraffin, and cut into sections (5 mm thick) for staining. The objective assessment of alveolarization of neonatal lungs was determined by the mean linear intercept method (Hasleton (1976) Patho. Eur. 11:211-8; Shaffer, et al. (1987) Pediatr. Res. 21:14-20). After exposure to HO, lung mean linear intercept (MLI) in Sphk1$^{-/-}$ is significantly lower compared with wild-type. *P<0.05 (n=5 to 8 per group). FIG. 7D, human lung microvascular endothelial cells (HLMVECs) grown to approximately 90% confluence were pre-incubated with 1 to 10 mmol/L SKI-II (SphK1/SphK2 inhibitor) in serum-free or media containing 1% FBS, as indicated for 24 hours before stimulation with hyperoxia (95% $O_2$ and 5% $CO_2$) for 3 hours. After incubation, cells were washed twice with PBS at room temperature, and total reactive oxygen species (ROS) production was measured by DCFDA fluorescence. SKI-II blocked ROS production in HLMVECs under hyperoxia. Data were quantified based on the number of DCFDA pixels. Values for ROS production are means±SD from three independent experiments and normalized to percentage control.

DETAILED DESCRIPTION OF THE INVENTION

Figure 1A:
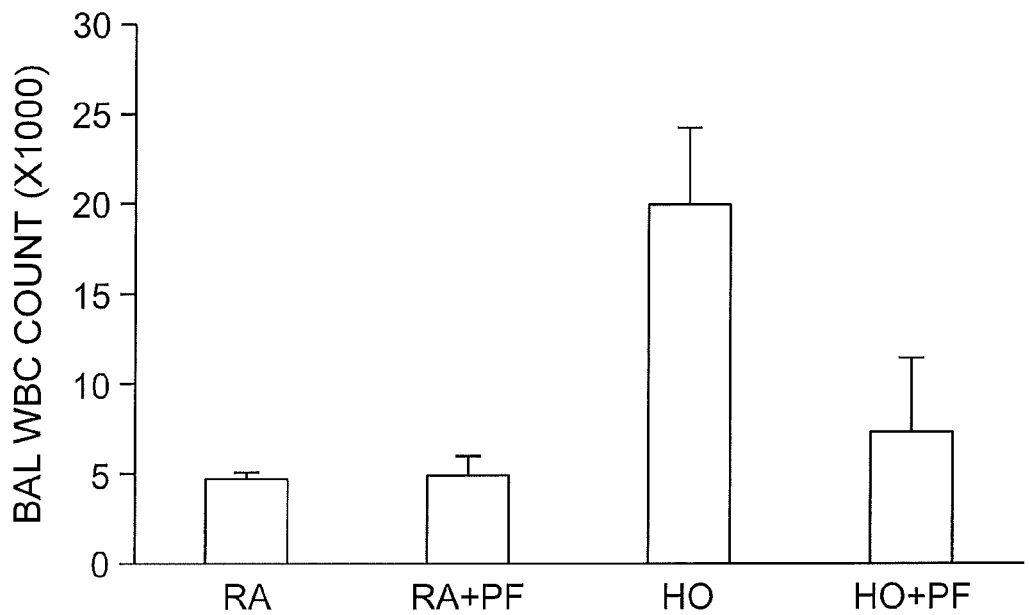
FIGS. 1A and 1B show that the Sphingosine Kinase 1 (SphK1) inhibitor, PF-543 (PF, 5 mg/kg/dose), decreases inflammatory cell infiltrate (bronchoalveolar lavage (BAL) white blood cell (WBC) count, FIG. 1A) and protein content (mg/ml, FIG. 1B) in the bronchoalveolar lung fluid in adult mice lungs following hyperoxia (HO) compared to mice exposed to room air (RA).

Based on expression analysis and animal model studies, it has now been shown that SphK1 is a novel therapeutic target for the prevention and treatment of a number of pulmonary diseases and conditions. In particular, it has been shown that exposure to hyperoxia increases expression of SphK1 and elevates S1P levels in neonatal lung tissue. In addition, SphK1$^{-/-}$ mice exposed to hyperoxia show improved alveolarization, and decreased ROS accumulation, protein expression of NOX2 and NOX4 and IL-6 levels. Further, SphK1 siRNA attenuates hyperoxia-induced S1P generation and ROS formation in HLMVECs and down-regulation of NOX2 or NOX4. Moreover, PF-543, a potent inhibitor of SphK1, ameliorates bleomycin-induced pulmonary fibrosis, prevents oxygen-induced lung injury and attenuates ROS generation in HLMVECs. This analysis demonstrates a correlation between the SphK/S1P signaling axis in lung injury and disease, and demonstrates that SphK1 is a therapeutic target against pulmonary diseases and conditions and oxygen-induced lung injury.

Therefore, this invention provides compositions and methods for preventing or treating a pulmonary disease or condition and/or oxygen-induced lung injury in a subject. The method involves administering to a subject in need of treatment an effective amount of a SphK1 inhibitor to prevent or treat the subject's pulmonary disease or condition or oxygen-induced lung injury. As used herein, "treat" or "treating" means to ameliorate, reverse, relieve, slow down, or alleviate one or more symptoms associated with the referenced disease or condition, whereas "prevent" or "preventing" means to lessen, delay, arrest development or mitigate at least one symptom of the referenced disorder. For the purposes of this invention, a subject can be an infant, child or adult and can include a human or non-human animal such as a companion animal, farm animal, or ranch animal.

In accordance with prophylactic administration of a SphK1 inhibitor, a subject in need of treatment refers to a subject at risk of having or at risk of developing a pulmonary disease or condition, e.g., a subject having one or more risk factors or having increased susceptibility or a predisposition for developing a pulmonary disease or condition. Risk factors known in the art include, but are not limited to, a history of tobacco smoking; exposure to an excess supply of oxygen (i.e., hyperoxia); long term exposure to one or more of organic dust, inorganic dust, chemical fumes, smoke; exposure to one or more allergens or infectious agents as well as a history of sepsis, pneumonia, trauma, lung contusion, drug abuse or overdose. An increased susceptibility or a predisposition for developing a pulmonary disease or condition includes, e.g., a family history or genetic predisposition to developing the referenced disease or condition.

In accordance with therapeutic administration of a SphK1 inhibitor, a subject in need of treatment refers to a subject exhibiting one or more signs or symptoms of the disease or condition or oxygen-induced injury. Signs or symptoms of pulmonary diseases or conditions include, but are not limited to, cough, dyspnea, purulent sputum, fever, episodic wheezing, dilation of airways, scarring of airways, inflammation, excess mucus, smooth muscle hyperplasia, airway constriction, shortness of breath, cyanosis, fatigue, angina pectoris, fainting or syncope, and/or peripheral edema. A pulmonary disease or condition can be diagnosed by conventional exams and/or tests including, but not limited to arterial blood gas, blood tests, blood and urine cultures, bronchoscopy, chest x-ray, sputum cultures and analysis, echocardiogram, and pressure measurements.

Conditions, disorders, or diseases of the pulmonary system that can be prevented or treated in accordance with the present compositions and methods include, but are not limited to, pulmonary hypertension; adult respiratory distress syndrome (ARDS); restrictive lung disease; chronic obstructive pulmonary disease (COPD); bronchiectasis; bronchiolectasis; bronchiolitis; bronchitis; emphysema; diffuse interstitial or infiltrative lung diseases including, but not limited to, pneumoconiosis, hypersensitivity pneumonitis, Goodpasture's syndrome, idiopathic pulmonary hemosiderosis, collagen-vascular diseases, or pulmonary eosinophilia; serofibrinous pleuritis; suppurative pleuritis; hemorrhagic pleuritis; pleural effusions; idiopathic pulmonary fibrosis; hyperoxia or oxygen-induced lung injury including, but not limited to, bronchopulmonary dysplasia; injury due to drug or chemotherapeutic toxicity (e.g., toxicity due to treatment with bleomycin, cyclophosphamide, nitrofurantoin, methotrexate, combination 5-fluorouracil and oxaliplatinum therapy or the like); radiation-induced injury; or chemical injury, e.g., a chemical burn, smoke inhalation, exposure to a toxic substance, or chemically-induced pneumonia. In certain embodiments, the pulmonary disease or condition is oxygen-induced lung injury, bleomycin-induced pulmonary fibrosis, radiation-induced pulmonary fibrosis, idiopathic pulmonary fibrosis or bronchopulmonary dysplasia.

Treatment of a pulmonary disease or condition or oxygen-induced injury desirably results in an improvement of one or more parameters of lung function including, e.g., forced expiratory volume in one second (FEVi); forced volume vital capacity (FVC); FEVi/FVC; peak expiratory flow (PEF); forced expiratory flow 25%-50% or 25%-75% (average flow of air exiting the lung during the middle portion of the expiration); forced expiratory time (FET); total lung capacity (TLC); diffusing capacity, carbon monoxide (DLCO); or maximum voluntary ventilation. In a more specific embodiment, said administering results in improvement of one or more of said parameters of lung function (1) to 80% or more of expected; or (2) by at least 2%, 3%, 4%, 5%, 6%, 7%, 8%, 9%, 50%. In a more specific embodiment, the method involves identifying any of said parameters that, prior to administration, are less than 80% of expected values for an individual of the same height and weight, and assessing said parameters after said administering, wherein said administering results in improvement of one or more of said parameters of lung function (1) to 80% or more of expected; or (2) by at least 2%, 3%, 4%, 5%, 6%, 7%, 8%, 9%, 50%.

SphK1 inhibitors of use in the prophylactic or therapeutic method and composition of this invention include SphK1 inhibitors that are cell permeable or membrane permeable, have an $IC_{50}$ value of less than 10 µM, have a $K_i$ of less than 10 µM, and/or exhibit at least a 20-fold greater selectivity for SphK1 than SphK2. In one embodiment, the SphK1 inhibitor is cell permeable, has an $IC_{50}$ value of less than 10 µM and a $K_i$ of less than 10 µM, but does not exhibit at least a 20-fold greater selectivity for SphK1 than SphK2. In another embodiment, the SphK1 inhibitor is cell permeable, has a $K_i$ of less than 10 µM, and has at least a 20-fold greater selectivity for SphK1 than SphK2, but has an $IC_{50}$ value greater than 10 µM. In a further embodiment, the SphK1 inhibitor has at least a 20-fold greater selectivity for SphK1 than SphK2, has an $IC_{50}$ value of less than 10 µM and a $K_i$ of less than 10 µM, but is not cell permeable. In another embodiment, the SphK1 inhibitor is cell permeable, has an $IC_{50}$ value of less than 10 µM, has at least a 20-fold greater selectivity for SphK1 than SphK2, but does not have a $K_i$ of less than 10 µM. In yet a further embodiment, the SphK1 inhibitor is cell permeable, has an $IC_{50}$ value of less than 10 µM, has a $K_i$ of less than 10 µM and has at least a 20-fold greater selectivity for SphK1 than SphK2.

An SphK1 inhibitor is cell permeable or membrane permeable when the inhibitor is capable of penetrating or being actively or passively transported across a cell membrane, i.e., being transferred from one side of a cell membrane to another side, e.g., entering into a cell from the outside of the cell by penetrating the cell membrane. In particular, a cell permeable SphK1 inhibitor can traverse a cell membrane in vitro or in vivo in the absence of a carrier or agent that facilitates membrane transport. In particular, embodiments, the SphK1 inhibitor is capable of traverse the cellular membrane of a pulmonary cell. In other embodiments, the SphK1 inhibitor is capable of penetrating cells intact and retains biological activity after penetrating the cells. The cell-penetrating function of a SphK1 inhibitor can be determined by methods known in the art, for example, by administration of the SphK1 inhibitor to an experimental animal and detecting the amount of the inhibitor present in pulmonary cells.

In another embodiment, a SphK1 inhibitor of the invention has a half maximal (50%) inhibitory concentration ($IC_{50}$) value of less than 10 μM. $IC_{50}$ values may be determined using techniques that are well-known in the art, for example, a dose-response curve that correlates the concentration of a compound or substance to the desired response in a cell, in this case SphK1 inhibition. In some embodiments, the SphK1 inhibitor has an $IC_{50}$ value in the range of 0.1 nM to 10 μm, in the range of 0.1 nM to 100 nM, in the range of 0.1 nM to nM, or in the range of 0.1 nM to 10 nM. In certain embodiments, the SphK1 inhibitor has an $IC_{50}$ value of less than or equal to 10 μM, 1 μM, 100 nM, 50 nM, 10 nM, 5 nM, 4 nM, 3 nM or 2 nM.

In a further embodiment, a SphK1 inhibitor of the invention has an inhibition constant ($K_i$) of less than 10 μM. As is known in the art, $K_i$ is the concentration required to produce half maximum inhibition ($K_i=[I]/(K'_M/K_M-1)$, wherein $K_M$ of sphingosine at SphK1=10 μM) and is an indication of how potent an inhibitor is. In some embodiments, the SphK1 inhibitor has a $K_i$ in the range of 1 nM to 10 μm, in the range of 1 nM to 100 nM, in the range of 1 nM to 50 nM, or in the range of 1 nM to 10 nM. In certain embodiments, the SphK1 inhibitor has a $K_i$ of less than or equal to 10 μM, 1 μM, 100 nM, 50 nM, 10 nM, 5 nM, 4 nM, 3 nM or 2 nM.

In yet a further embodiment, a SphK1 inhibitor of this invention exhibits at least a 20-fold greater selectivity for SphK1 than SphK2. In particular, compounds useful in the compositions and methods of this invention can have at least a 20, 30, 40, 50, 60, 70, 80, 90, 100, 200, 300 or greater fold selectivity for SphK1 compared to SphK2. A SphK1 inhibitor is selective if it inhibits SphK1 but fails to inhibit, or inhibits to a substantially lesser degree SphK2. Methods for assessing the selectively of SphK inhibitors are known in the art and can be based upon any conventional assay including, but not limited to $IC_{50}$ determinations, as well as determining the $K_i$, and/or the half maximal effective concentration ($EC_{50}$) of the inhibitor for SphK1 as compared to SphK2. By way of illustration, selectivity can be expressed as $(K_i/K_M)^{SphK2}/(K_i/K_M)^{SphK1}$. In addition to selectivity for SphK1 over SphK2, in certain embodiments, the inhibitor also exhibits selectivity for SphK1 over other sphingolipid-metabolizing enzymes such as ceramide synthase and S1P lyase and selectivity over one or more of ERK2, PI3K, PKCα, PKCδ, PKA, Akt1, ERK1, EGFR, CDK2, IKKβ, and CamKIIβ. In this respect, the SphK1-selective inhibitor does not exhibit off-target effects, e.g., it does not inhibit DNA synthesis.

SphK1 inhibitors of use in this invention include, e.g., [(2R)-1-[[4-[[3-(benzenesulfonyl methyl)-5-methylphenoxy]methyl]phenyl]methyl] pyrrolidin-2-yl] methanol (PF-543) or an analog, derivative or pharmaceutically acceptable salt thereof.

PF-543 is a cell-permeable hydroxymethylpyrrolidine compound that inhibits sphingosine kinase-1/SphK1-catalyzed sphingosine phosphorylation ($IC_{50}$=2.0 nM; [sphingosine] =3 μM) in a reversible and sphingosine-competitive manner ($K_i$=3.6 nM). PF-543 does not exhibit any affinity toward S1P receptors and has about 130-fold greater selectivity for Sphk1 over SphK2 ($IC_{50}$=356 nM). PF-543 directly targets SphK1 ($K_d$=5 nM) with 1:1 stoichiometry. See, e.g., Schnute, et al. (2012) *Biochem. J.* 444:79-88. PF-543 is commercially available, for example from ApexBio Technology (Boston, Mass.) and Selleck Chemicals (Houston, Tex.).

The term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

The term "derivative" refers to compounds that have a common core structure, and are substituted with one or more functional groups.

A "pharmaceutically acceptable salt" refers to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

All references to pharmaceutically acceptable salts include solvent addition forms (solvates) or crystal forms (polymorphs) as defined herein, of the same salt. Pharmaceutically acceptable salts of the present invention can be synthesized from a parent compound that contains a basic or

PF-543

acidic moiety by conventional chemical methods. Generally, such salts can be prepared by reacting the free acid or base forms of these compounds with a stoichiometric amount of the appropriate base or acid in water or in an organic solvent, or in a mixture of the two; non-aqueous media like ether, ethyl acetate, ethanol, isopropanol, or acetonitrile can be used. Lists of suitable salts are found in Remington: The Science and Practice of Pharmacy, 22$^{nd}$ ed. (Pharmaceutical Press, 2012). For example, salts can include, but are not limited to, the hydrochloride and acetate salts of the aliphatic amine-containing, hydroxyl amine-containing, and imine-containing compounds of the present invention. In particular embodiments, the salt is a citric acid salt.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

Additional SphK1 inhibitors of use in the compositions and methods of the invention are known in the art. See, for example, U.S. Pat. Nos. 8,557,800, 8,436,186 and 8,372,888, incorporated herein by reference and US 2012/0252815, US 2012/0214858, WO 2014/118556 and WO 2014/157382 as well as the references cited therein. Various chemically synthesized short-chain sphingosine and dihydrosphingosine analogs serve as inhibitors of SphK (Edsall, et al. (1998) Biochemistry 37:12892-8; DeJonghe, et al. (1999) Bioorg. Med. Chem. Lett. 9:3175-3180; Johnson, et al. (2004) J. Pharmacol. Exp. Ther. 309:452-461; Niro, et al. (2004) Bioorg. Med. Chem. 12:45-51). It was found that replacement of the alkyl chain with a phenyl ring or substituting fluorine for the 3-hydroxyl group yielded potent SphK inhibitors. Further, analogs with a 4,5-trans double bond were generally superior inhibitors (DeJonghe, et al. (1999) Bioorg. Med. Chem. Lett. 9:3175-3180). Moreover, the importance of a 4-hydroxypiperidinyl group in the selective inhibition of SphK1 has been demonstrated (Baek, et al. (2013) Chem. Commun. 49:2136-2138; Gustin, et al. (2013) Bioorg. Med. Chem. Lett. 23:4608-4616).

More specifically, SphK1 selective inhibitors include, but are not limited to, SKI 5C ($IC_{50}$=3.3 µM), BML-258 ($K_i$=~10 µM), Compound 1 ($K_i$=0.2 µM, 5-fold selectivity for SphK1 over SphK2), Compound 2 ($K_i$=0.3 µM, 40-fold selectivity for SphK1 over SphK2), Compound 3 ($K_i$=75 nM, 80-fold selectivity for SphK1 over SphK2), Compound 4 ($K_i$=110 nM, 470-fold selectivity for SphK1 over SphK2), Compound 5 ($K_i$=47 nM, 180-fold selectivity for SphK1 over SphK2), RB-005 ($IC_{50}$=3.6 µM), VPC96091 ($K_i$=0.1 µM, 15-fold selectivity for SphK1 over SphK2) and Compound 55-21 ($IC_{50}$=7.1 µM, ~108-fold selectivity for SphK1 over SphK2). See, e.g., Kennedy, et al. (2011) J. Med. Chem. 54:3524-48; Baek, et al. (2013) J. Med. Chem. 56:9310-27; DeJonghe, et al. (1999) Bioorg. Med. Chem. Lett. 9:3175-3180; and Byun, et al. (2013) Med. Chem. Commun. 4:1394.

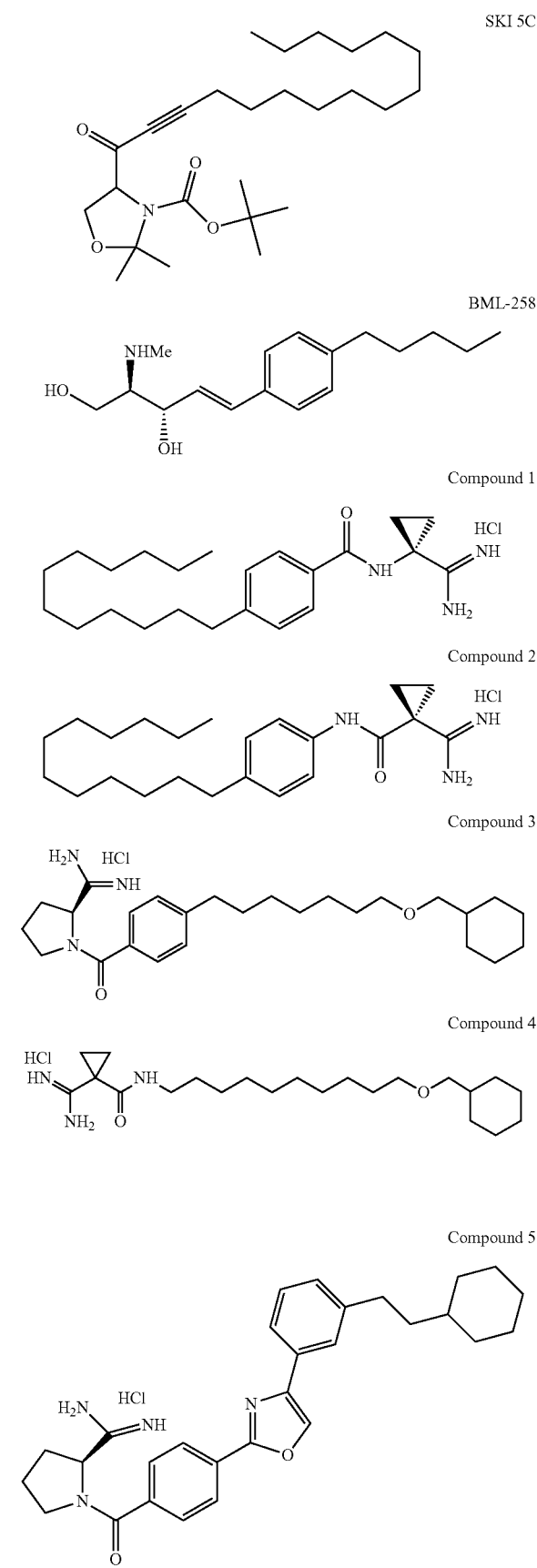

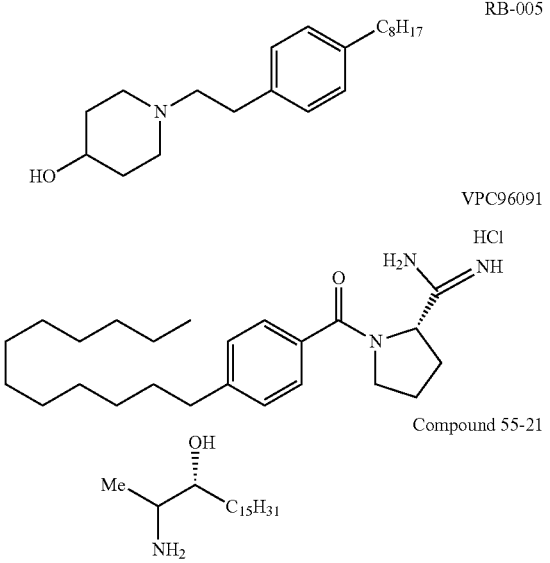

This invention also provides a pharmaceutical composition containing one or more of the SphK1 inhibitors described herein together with one or more pharmaceutically acceptable vehicles, and optionally one or more other therapeutic and/or prophylactic ingredients. The term "pharmaceutically acceptable vehicle" refers to a diluent, adjuvant, excipient or carrier with which an inhibitor of the disclosure is administered. The term "effective amount" or "pharmaceutically effective amount" refers to a nontoxic but sufficient amount of the inhibitor to provide the desired biological result. That result can be reduction and/or alleviation of the signs, symptoms, or causes of a disease, or any other desired alteration of a biological system. An appropriate "effective" amount in any individual case can be determined by one of ordinary skill in the art using routine experimentation.

Pharmaceutically acceptable vehicles for therapeutic use are well-known in the pharmaceutical art, and are described, for example, in *Remington: The Science and Practice of Pharmacy*, $22^{nd}$ ed. (Pharmaceutical Press, 2012). For example, sterile saline and phosphate-buffered saline at physiological pH can be used. Preservatives, stabilizers, dyes and even flavoring agents can be provided in the pharmaceutical composition. For example, sodium benzoate, sorbic acid and esters of p-hydroxybenzoic acid can be added as preservatives. In addition, antioxidants and suspending agents can be used.

Suitable excipients for non-liquid formulations are also known to those of skill in the art. A thorough discussion of pharmaceutically acceptable excipients and salts is available in *Remington: The Science and Practice of Pharmacy*, $22^{nd}$ ed. (Pharmaceutical Press, 2012).

Additionally, auxiliary substances, such as wetting or emulsifying agents, biological buffering substances, surfactants, and the like, can be present in such vehicles. A biological buffer can be any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, pharmaceutical compositions can be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected inhibitor in combination with a pharmaceutically acceptable vehicle and, in addition, can include other pharmaceutical agents, adjuvants, diluents, buffers, and the like.

In general, the compositions of the disclosure will be administered in a therapeutically effective amount by any of the accepted modes of administration. Suitable dosage ranges depend upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compositions of the disclosure for a given disease.

Thus, the compositions of the disclosure can be administered as pharmaceutical formulations including those suitable for oral (including buccal and sub-lingual), rectal, nasal, topical, pulmonary, vaginal or parenteral (including intramuscular, intra-arterial, intrathecal, subcutaneous and intravenous) administration or in a form suitable for administration by inhalation or insufflation. In some embodiments, administration is via intravenous or oral routes using a convenient daily dosage regimen, which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see *Remington: The Science and Practice of Pharmacy*, referenced above.

For cell impermeable compounds, permeation enhancers can be used including polymers such as polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

For oral administration, the composition will generally take the form of a tablet, capsule, a softgel capsule or can be an aqueous or nonaqueous solution, suspension or syrup. Tablets and capsules are preferred oral administration forms. Tablets and capsules for oral use can include one or more commonly used carriers such as lactose and corn starch. Lubricating agents, such as magnesium stearate, are also typically added.

Typically, the compositions of the disclosure can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a patient through a needle or a catheter, propelled by a sterile syringe or some other mechanical device such as an continuous infusion system. A formulation provided by the disclosure can be administered using a syringe, injector, pump, or any other device recognized in the art for parenteral administration.

Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Preparations according to the disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Sterile injectable solutions are prepared by incorporating one or more of the compounds of the disclosure in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Alternatively, the pharmaceutical compositions of the disclosure can be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols.

Preferred formulations for topical drug delivery are ointments and creams. Ointments are semisolid preparations which are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Formulations for buccal administration include tablets, lozenges, gels and the like. Alternatively, buccal administration can be effected using a transmucosal delivery system as known to those skilled in the art. The compounds of the disclosure can also be delivered through the skin or muscosal tissue using conventional transdermal drug delivery systems, i.e., transdermal "patches" wherein the agent is typically contained within a laminated structure that serves as a drug delivery device to be affixed to the body surface. In such a structure, the drug composition is typically contained in a layer, or "reservoir," underlying an upper backing layer. The laminated device can contain a single reservoir, or it can contain multiple reservoirs. In one embodiment, the reservoir includes a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, can be either a polymeric matrix as described above, or it can be a liquid or gel reservoir, or can take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

In particular embodiments, the SphK1 inhibitors of the disclosure are formulated for aerosol administration, particularly to the respiratory tract and including intranasal administration. In order to assure proper particle size in a liquid aerosol, particles can be prepared in respirable size and then incorporated into a colloidial dispersion either containing a propellant as a metered dose inhaler (MDI) or air, such as in the case of a dry powder inhaler (DPI). The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The dose of drug can be controlled by a metered valve. Alternatively, the active ingredients can be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition can be presented in unit dose form for example in capsules or cartridges of, e.g., gelatin or blister packs from which the powder can be administered by means of an inhaler. Alternatively, formulations can be prepared in solution form in order to avoid the concern for proper particle size in the formulation. Solution formulations must nevertheless be dispensed in a manner that produces particles or droplets of respirable size.

For MDI application, an aerosol formulation is filled into an aerosol canister equipped with a metered dose valve. In the hands of the patient or subject the formulation is dispensed via an actuator adapted to direct the dose from the valve to the patient or subject.

Generally, formulations for aerosol administration can be prepared by combining (i) the selected drug or drugs in an amount sufficient to provide a plurality of therapeutically effective doses; (ii) the fluid, e.g., propellant, in an amount sufficient to propel a plurality of doses, e.g., from an aerosol canister; (iii) optionally, the water addition in an amount effective to further stabilize each of the formulations; and (iv) any further optional components, e.g., ethanol as a cosolvent; and dispersing the components. The components can be dispersed using a conventional mixer or homogenizer, by shaking, or by ultrasonic energy as well as by the use of a bead mill or a microfluidizer. Bulk formulations can be transferred to smaller individual aerosol vials by using valve to valve transfer methods, pressure filling or by using conventional cold-fill methods. It is not required that a component used in a suspension aerosol formulation be soluble in the fluid carrier, e.g., propellant. Components that are not sufficiently soluble can be coated or congealed with polymeric, dissolution controlling agents in an appropriate amount and the coated particles can then be incorporated in a formulation as described above. Polymeric dissolution controlling agents suitable for use in this invention include, but not limited to polylactide glycolide co-polymer, acrylic esters, polyamidoamines, substituted or unsubstituted cellulose derivatives, and other naturally derived carbohydrate and polysaccharide products such as zein and chitosan.

Where a macromolecular medicament is employed, optionally a suitable second stabilizer is selected. A suitable second stabilizer is a protective colloid such as glycin, glycine, alanine, valine, leucine, isoleucine, leucylalanine, methionine, threonine, isovaline, phenylalanine, tyrosine, serine, cysteine, N-acetyl-L-cysteine, histidine, tryptophan, proline, and hydroxyproline, e.g., trans-4-hydroxy proline, aspartic acid, and glutamic acid, arginine, glutamine, lysine, hydroxylysine, ornithine, asparagine, citrulline and the like.

A fluid or aerosol formulation preferably includes the protective colloid stabilizer in an amount effective to stabilize the formulation relative to an identical formulation not containing the stabilizer, such that the drug does not settle, cream or flocculate after agitation so quickly as to prevent reproducible dosing of the drug. Reproducible dosing can be achieved if the formulation retains a substantially uniform drug concentration for about fifteen seconds to about five minutes after agitation.

Typically, for optimal functional and therapeutic performance of an aerosol formulation, either as a dry powder or as an aerosol suspension, the stabilizer is present either as a coarse carrier (e.g., 20-90 μm) or as a finely micronized powder, ≤0 μm in diameter. In either case, reproducible drug dosimetry is obtained without the need to qualify the inspiratory maneuver of the patient. Accordingly, excellent dose uniformity is obtained at tidal flows of up to 2 liters, or at inspiratory flow rates of as low as 15 liters per minute to about 90 liters per minute.

The particular amount of stabilizer that constitutes an effective amount is dependent upon the particular stabilizer, the particular propellant, and on the particular drug used in the formulation. It is therefore not practical to enumerate specific effective amounts for use with specific formulations of the invention, but such amounts can readily be determined by those skilled in the art with due consideration of the factors set forth above. Generally, however, the protective colloid stabilizer can be present in a formulation in an amount from about 0.0001 parts per million to about 200,000 parts per million, more preferably about 1 part per million to about 10,000 parts per million, most preferably from about 10 parts per million to about 5,000 parts per million of the total formulation.

Aerosol canisters equipped with conventional valves, preferably metered dose valves, can be used to deliver the formulations of the invention. It has been found, however, that selection of appropriate valve assemblies for use with aerosol formulations is dependent upon the particular component and other adjuvants used (if any), on the fluid, e.g., propellant, and on the particular drug being used. Conventional neoprene and buna valve rubbers used in metered dose valves for delivering conventional chlorofluorocarbon formulations often have less than optimal valve delivery characteristics and ease of operation when used with formulations containing HFC-134a or HFC-227 propellant. Therefore certain formulations of the invention are preferably dispensed via a valve assembly wherein the diaphragm is made of a nitrile rubber such as DB-218 (American Gasket and Rubber; Schiller Park, Ill.) or an EPDM rubber such as VISTALON (Exxon), ROYALENE (UniRoyal), BUNAEP (Bayer). Also suitable are diaphragms fashioned by extrusion, injection, molding or compression molding from a thermoplastic elastomeric material, such as FLEXOMER GERS 1085 NT polyolefin (Union Carbide).

Conventional aerosol canisters, coated or uncoated, anodized or unanodized, e.g., those of aluminum, glass, stainless steel, polybutyl or polyethylene terephthalate, and coated canisters or cans with epon, epoxy, etc., can be used to contain a formulation of the invention.

A pharmaceutically or therapeutically effective amount of the composition will be delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. Thus, the effective amount for a given situation can be determined by routine experimentation. For purposes of the disclosure, generally a therapeutic amount will be in the range of about 0.01 mg/kg to about 250 mg/kg body weight, more preferably about 0.1 mg/kg to about 10 mg/kg, in at least one dose. In larger mammals the indicated daily dosage can be from about 1 mg to 300 mg, one or more times per day, more preferably in the range of about 10 mg to 200 mg. The subject can be administered as many doses as is required to reduce and/or alleviate the signs, symptoms, or causes of the disorder in question, or bring about any other desired alteration of a biological system. When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The following non-limiting examples are provided to further illustrate the present invention.

EXAMPLE 1

Involvement of SphK1 in Pulmonary Fibrosis

Idiopathic pulmonary fibrosis (IPF) is a devastating disease characterized by alveolar epithelial cell injury, accumulation of fibroblasts/myofibroblasts and deposition of extracellular matrix proteins. It has been demonstrated that levels of S1P are elevated in bronchoalveolar fluids and lung tissues from IPF patients and animal models of pulmonary fibrosis. Microarray analysis of blood mononuclear cells from patients with IPF and SphK1-, SphK2- or S1PL-knockout mice and SphK inhibitor, SKI-II (4-[[4-(4-chlorophenyl)-2-thiazolyl]amino]-phenol) have been used to assess the role of S1P in fibrogenesis. The expression of SphK1 negatively correlates with lung function and survival of patients with IPF. Further, the expressions of SphK1 and S1PL are increased in lung tissues from patients with IPF and bleomycin-challenged mice. Genetic knockdown of SphK1, but not SphK2, ameliorates bleomycin-induced pulmonary fibrosis in mice while deletion of S1PL (SGPL1$^{+/-}$) in mice potentiates fibrosis post-bleomycin challenge. TGF-β increases the expression of SphK1 and S1PL in human lung fibroblasts and knockdown of SphK1 or treatment with SphK inhibitor SKI-II attenuates S1P generation and TGF-β-mediated signal transduction. Over-expression of S1PL attenuates bleomycin-induced TGF-β secretion and S1P-mediated differentiation of human lung fibroblasts through regulation of autophagy. Administration of SphK inhibitor SKI-II eight days post-bleomycin challenge reduces bleomycin-induced mortality and pulmonary fibrosis. See Huang, et al. (2013) *FASEB J.* 27:1749-60; Huang & Natarajan (2015) *Adv. Biol. Reg.* 57:55-63; Huang, et al. (2015) *Thorax* doi:10.1136/thoraxjnl-2014-206684.

EXAMPLE 2

PF-543 Ameliorates Bleomycin-Induced Pulmonary Fibrosis

In Vivo Studies. In this analysis, 8 week-old, wild-type, C57BL/6J mice were treated with 1.5 U/kg bleomycin. Subsequently, the mice were administered PF-543 (i.p., 5 mg/kg; twice per week) from day 7 to 21 days post-bleomycin challenge. The results of this analysis indicated that PF-543 partly protected mice against lung injury, and pulmonary fibrosis as evidenced by decreased total collagen deposition, TGF-β levels in bronchoalveolar lavage (BAL) fluids, expression of α-smooth muscle actin (α-SMA) and fibronectin in lung tissues as compared to bleomycin-challenged mice without PF-543.

In a similar study, PF-543 was administered (i.p., 5 mg/kg; twice per week) from day 21 to 42 days post-bleomycin (8 weeks old wild-type, C57BL/6J mice; 1.5 U/kg) challenge. This analysis indicated enhanced resolution of pulmonary fibrosis as evidenced by a decrease in collagen deposition and Ashcroft's score compared to bleomycin-challenged mice without PF-543.

In Vitro Studies. To further analyze the effects of PF-543, human lung fibroblasts were treated with PF-543 (1-5 µM) for 1 hour and TGF-β-mediated differentiation was assessed. This analysis indicated that PF-543 attenuated TGF-β-mediated fibroblast differentiation to myofibroblasts as evidenced by decreased expression of fibronectin and α-SMA. In addition, pretreatment of fibroblasts with PF-543 attenuated TGF-β-induced expression of YAP1, a transcriptional factor associated with fibroblast to myofibroblast differentiation.

The involvement of SphK1 in regulating TGF-β-induced YAP1 expression in lung fibroblasts was further analyzed in SphK1$^{-/-}$ mice. TGF-β (5 ng/ml for 48 hours) was administered to SphK1$^{-/-}$ mice and YAP1 expression was measured. This analysis indicated that TGF-β-mediated up-regulation of YAP1 expression was reduced in mouse lung fibroblasts isolated from SphK1$^{-/-}$ mice compared to cells from wild-type mice. These results indicate a role for SphK1 in YAP1 expression.

Normal human lung fibroblasts, pretreated with PF-543 (1-5 µM in DMSO) or vehicle (DMSO) for 1 hour, were further treated with TGF-β (5 ng/ml, 48 hours). TGF-β- induced fibroblast differentiation was characterized to analyze the expression of fibronectin and α-SMA. The data indicated that pretreatment with PF-543 (1, 5 µM) dramatically inhibited TGF-β-induced expression of fibronectin and α-SMA, as well as cell differentiation of human lung fibroblasts. Interestingly, TGF-β also increased the expression of YAP1, the key protein in the hippo/Yap pathway; and the treatment of PF-543 also dramatically inhibited TGF-β-induced expression of YAP1 in human lung fibroblasts. Additionally, compared with the control mouse lung fibroblast (from wild-type mice), TGF-β-induced fibroblast differentiation and expression of YAP1 were dramatically lower in the lung fibroblast isolated from SphK1$^{-/-}$ mice. Accordingly, selective inhibition of SphK1 is useful in the prevention and treatment of bleomycin-induced pulmonary fibrosis.

EXAMPLE 3

PF-543 in the Prevention and Treatment of Oxygen-Induced Lung Injury

Figure 1B:
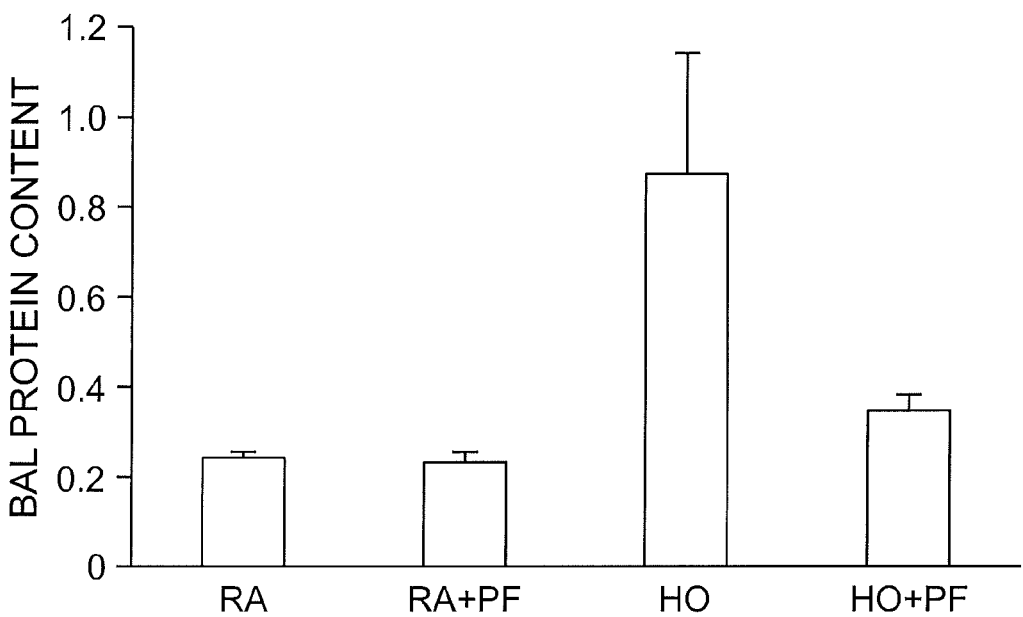

To demonstrate the use of PF-543 in attenuating hyperoxia-induced adult lung injury, a dose of 5 mg/kg/d PF-543×2 days was administered to adult mice prior to exposure to oxygen (75%). This analysis indicated that PF-543 attenuated hyperoxia-induced lung injury as evidenced by lung histology and bronchoalveolar lavage (BAL) findings. Lung histology showed reduced lung inflammatory fluid infiltration following treatment with PF-543. BAL fluid showed reduced total protein concentration and reduced inflammatory cell infiltrate. See FIGS. 1A and 1B.

Figure 2A:
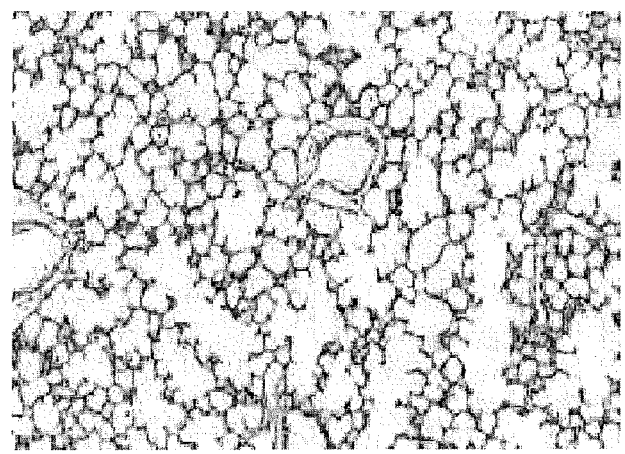
FIGS. 2A-2C show that PF-543 protects lungs when administered to newborn mice prior to and during hyperoxia exposure. Newborn mice exposed to room air (FIG. 2A) were compared to newborn mice exposed to hyperoxia (75%) (FIG. 2B) or exposed to hyperoxia (75%) and given PF-543 (20 mg/kg/day) (FIG. 2C). Lung structure is well preserved in the PF-543 treatment group (FIG. 2C).
Figure 2B:
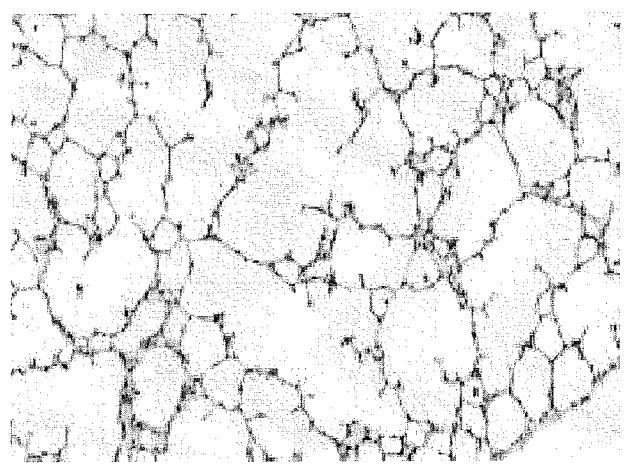
Figure 2C:
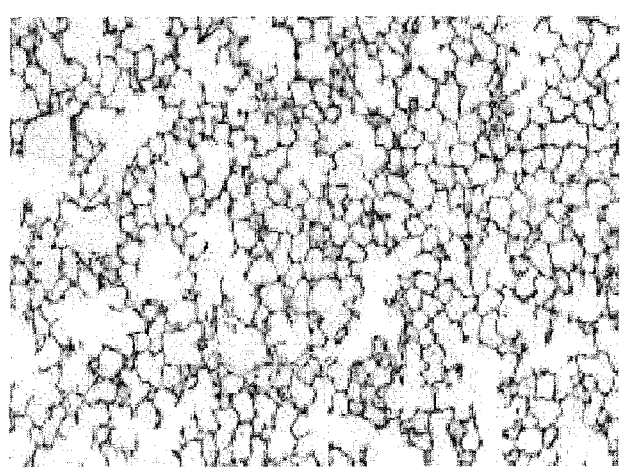

In similar analyses, newborn mice were exposed to room air, hyperoxia (75%) or hyperoxia (75%) subsequent to administration of PF-543 (20 mg/kg/day). This analysis indicated that the lungs of newborn mice exposed to oxygen (75%) exhibited significant damage similar to emphysema, whereas the lung structure of those animals pretreated with PF-543 and exposed to oxygen (75%) was well preserved (FIGS. 2A-2C). Therefore, PF-543 protected the lungs of the newborn mice from oxygen injury.

To demonstrate the use of PF-543 in the treatment of lung injury from hyperoxic insult, PF-543 is administered 24 hours or 12 hours after start of exposure of neonatal mouse pups or adult mice, respectively to hyperoxia.

Figure 3A:
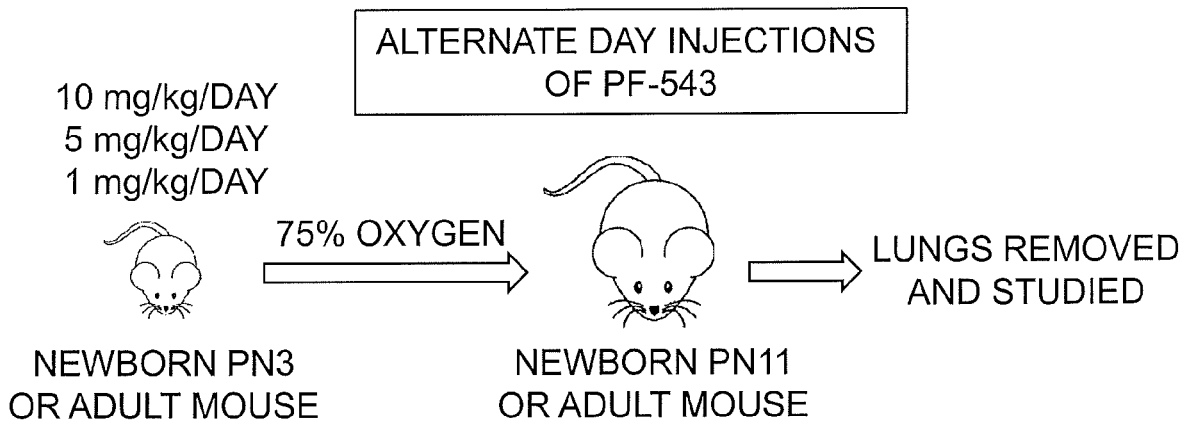
FIGS. 3A-3C demonstrate protocols for determining optimum dose (FIG. 3A), and drug efficacy when administered locally (FIG. 3B) and in an animal model of COPD (FIG. 3C).

To determine the lowest efficacious dose, PF-543 is administered systemically by injection, or locally to the lungs. For systemic administration (FIG. 3A), three different low doses of PF-543 (i.e., 1 mg/kg, 5 mg/kg and 10 mg/kg) are used in adult and newborn mice (PN3) to identify the most efficacious dose against hyperoxic lung injury. PF-543 is administered for 7 days to newborn mice and 3 days to adult via alternate day injections. Lung damage is assessed based on histology, protein and cytokine levels, and differential cell counts in bronchoalveolar lavage fluids.

Figure 3B:
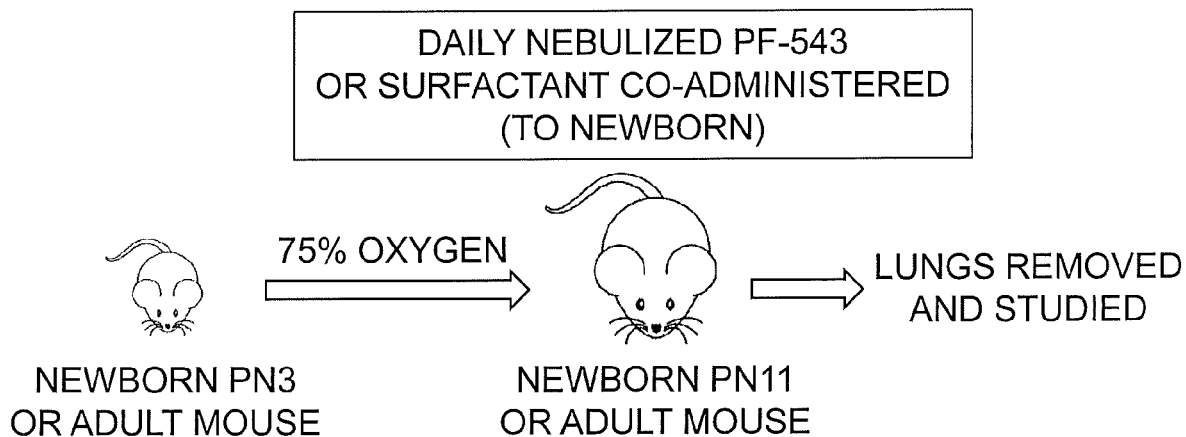

For local administration (FIG. 3B), PF-543 is aerosolized through a nebulizer or administered intranasally three times daily for the duration of treatment, i.e., 7 days for newborn mice and 3 days for adult mice. In newborn mice, PF-543 is administered both in the nebulized form and as an adjunct with commercial lung surfactant preparation. Surfactant is routinely administered to premature newborns as a treatment for respiratory distress syndrome. Surfactant is largely a mixture of synthetic lipids that mimics natural lung surfactant. PF-543 being lipid soluble can be easily administered to preterm newborns. PF-543 dissolved in surfactant is administered intranasally every day for 7 days to 3 day old mice pups that are exposed to hyperoxia at the same time. It is expected that locally administered PF-543 will dramatically increase the availability and potency of PF-543 thereby lowering the dose required to obtain the desired effect.

Figure 3C:
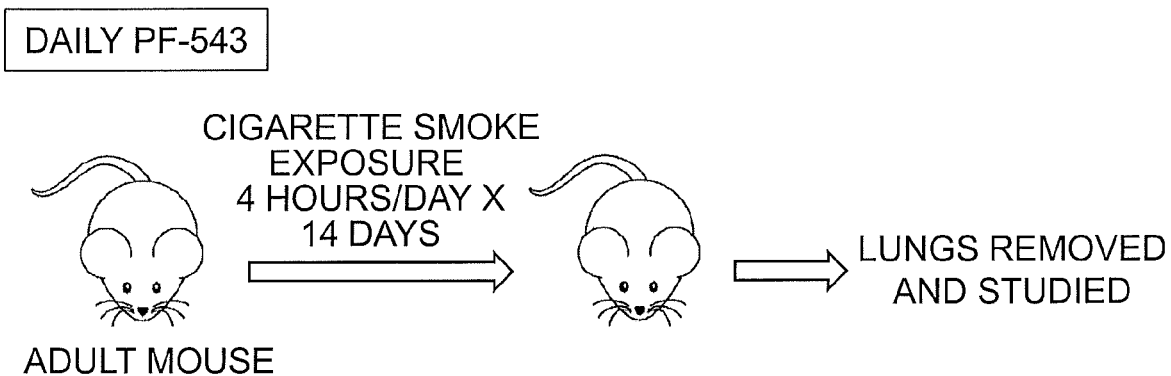

Cigarette smoke inhalation is a well-established animal model for COPD. Accordingly, to demonstrate the protective effect of PF-543 in COPD, adult mice are exposed to cigarette smoke and PF-543 is administered systemically or locally at an efficacious dose (FIG. 3C). Lung damage is assessed based on histology, protein and cytokine levels, and/or differential cell counts in bronchoalveolar lavage fluids. It is expected that PF-543 will protect the animals against lung injury in this model of COPD. Accordingly, based upon these experimental and expected results, selective inhibition of SphK1 is useful in the prevention and treatment of oxygen-induced lung injury.

EXAMPLE 4

PF-543 Attenuates ROS Generation in HLMVECs

It has been demonstrated that hyperoxia-induced ROS production is regulated by Src-dependent tyrosine phosphorylation of p47phox in HPAECs (Chowdhury, et al. (2005) *J. Biol. Chem.* 280:20700-11). However, the role of SphK1/S1P signaling in NADPH oxidase activation and ROS production was not shown. To demonstrate the role of SphK1, HLMVECs were pre-treated with PF-543 prior to exposure to hyperoxia. The results of this analysis indicated that PF-543 attenuated hyperoxia-mediated [$^{32}$P]S1P generation (>80%) compared to cells not treated with PF-543, thereby confirming the potency of the inhibitor. Subsequently, the effect of PF-543 on hyperoxia-induced p47phox translocation to cell periphery and ROS production was investigated. This analysis indicated that hyperoxia-induced p47phox translocation to cell periphery and ROS generation was inhibited by PF-543 compared with untreated cells. In contrast to hyperoxia, exogenous S1P-mediated translocation of p47phox to cell periphery was not affected by PF-543.

To further confirm the role of SphK1 in hyperoxia-mediated activation of p47phox, live cell imaging was performed using p47phox biosensor, a redox sensitive protein formed by fusion of redox sensitive GFP with p47phox (p47-roGFP). HLMVECs were transfected with p47-roGFP prior to exposure to hyperoxia. This analysis indicated that hyperoxia caused aggregation of GFP-tagged p47 vesicles in HLMVECs compared to normoxia, and PF-543 suppressed the hyperoxia-induced aggregation and stimulation of p47phox biosensor protein. These results show the dependency of SphK1 in hyperoxia-induced activation of p47phox and ROS generation in HLMVECs. Further, SphK1-specific inhibitor (PF-543) and siRNA of Spns2, S1P1 and S1P2 attenuated hyperoxia-induced activation of p47phox in HLMVECs; and inhibition of SphK1, using PF-543, did not affect exogenous S1P-induced p47phox activation.

EXAMPLE 5

Involvement of SphK1 in Radiation-Induced Pulmonary Fibrosis

Figure 4A:
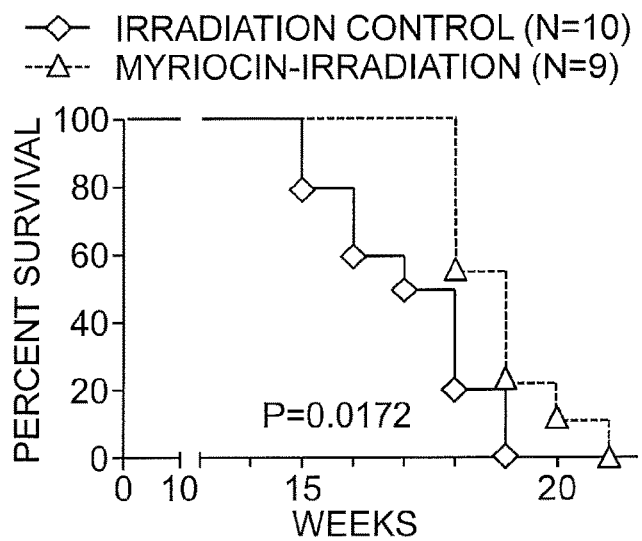
FIGS. 4A-4F show that myriocin decreases radiation-induced pulmonary inflammation, fibrosis, and upregulation of SphK1 activity and expression in mice administered a single thoracic dose (20 Gy) of irradiation.

In contrast to early post-irradiation period, it has been shown that late post-irradiation SphK1 and sphingoid base-1-phosphates are associated with radiation-induced pulmonary fibrosis (RIF). Using a mouse model, it has been demonstrated that RIF is characterized by a marked upregulation of sphingosine-1-phosphate (S1P) and dihydrosphingosine-1-phosphate (DHS1P) levels in the lung tissue and in circulation accompanied by increased lung SphK1 expression and activity. Inhibition of sphingolipid de novo biosynthesis by targeting serine palmitoyltransferase (SPT) with myriocin reduces radiation-induced pulmonary inflammation and delays the onset of RIF as evidenced by increased animal lifespan (FIG. 4A) and decreased expression of markers of fibrogenesis, such as collagen and α-SMA, in the lung. See Gorshkova, et al. (2012) *J. Lipid Res.* 53:1553-1568.

Figure 4B:
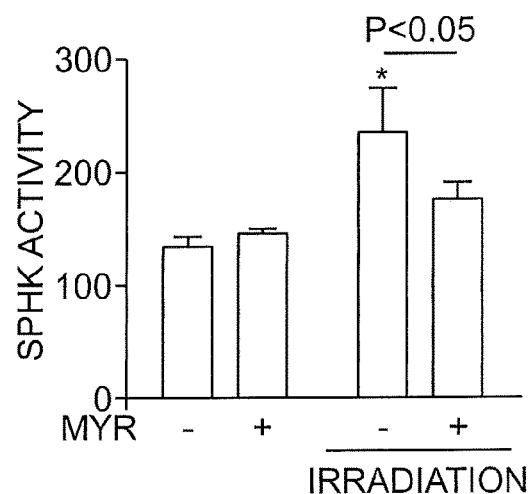
Figure 4C:
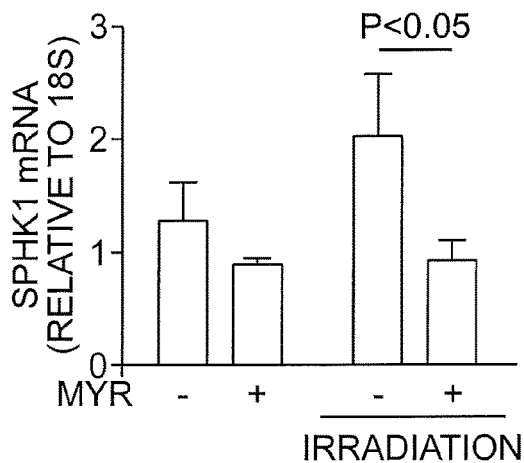
Figure 4D:
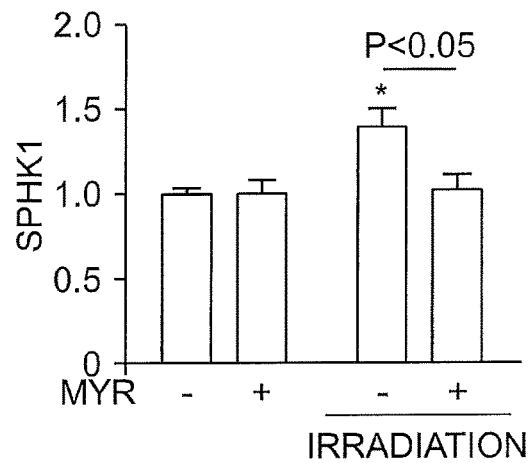
Figure 4E:
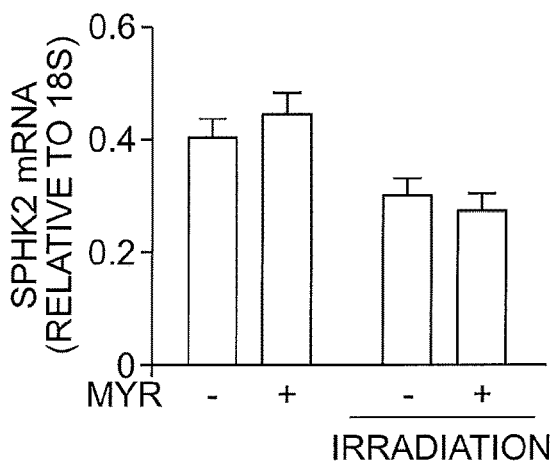
Figure 4F:
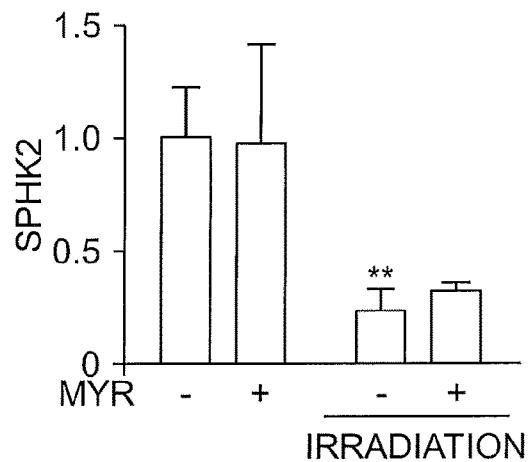

The effect of myriocin on the expression SphK1 and SphK2 has also been demonstrated. The evaluation of the total SphK activity in the lung tissue samples indicates a substantial (2-fold) increase by irradiation and the ability of myriocin to hinder this radiation-induced effect (FIG. 4B). The effect of myriocin on radiation-induced SphK activity is mirrored by its effect on SphK1 expression (FIGS. 4C and 4D) but not SphK2 expression (FIGS. 4E and 4F). See Gorshkova, et al. (2012) *J. Lipid Res.* 53:1553-1568. Therefore, the observed decrease in radiation-induced pulmonary inflammation and delay in the onset of RIF observed in response to myriocin correlates with a decrease in the expression and activity of SphK1, but not SphK2. Accordingly, selective inhibition of SphK1 is useful in the prevention and treatment of radiation-induced pulmonary fibrosis.

EXAMPLE 6

Involvement of SphK1 in Pulmonary Arterial Hypertension (PAH)

Figure 5A:
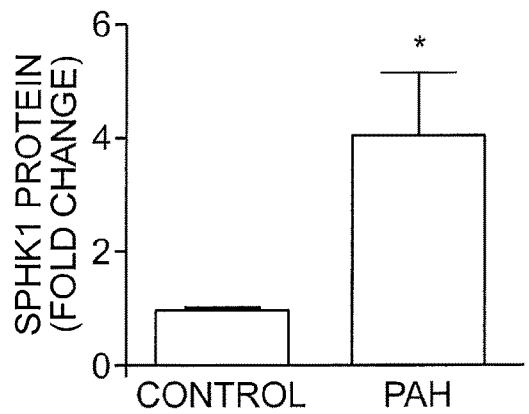
FIGS. 5A-5D show that SphK1 is increased in the lungs of patients and animal models of pulmonary arterial hypertension (PAH).
Figure 5B:
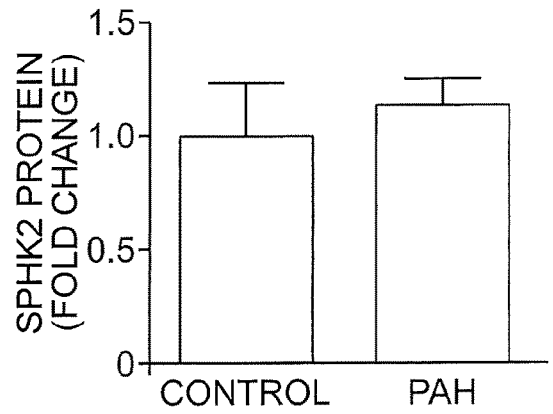
Figure 5C:
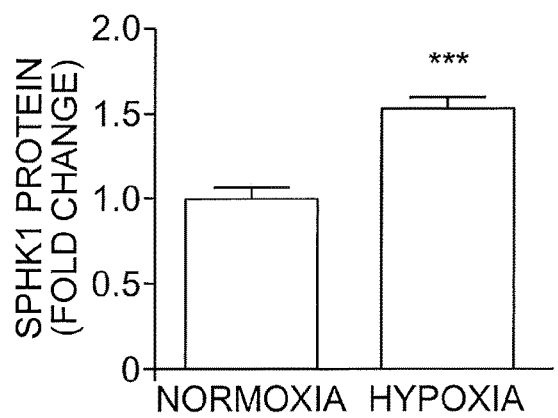
Figure 5D:
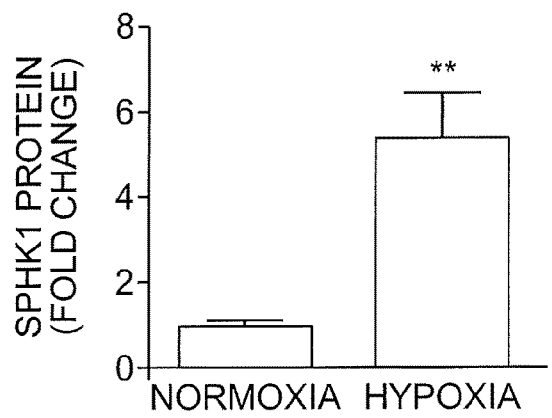

Protein levels of SphK1, but not SphK2, have been shown to be significantly elevated in the lungs (FIGS. 5A-5B) and pulmonary artery smooth muscle cells (PASMCs) of patients with PAH when compared with control subjects. A similar pattern has been observed in experimental rodent models of hypoxia-mediated pulmonary hypertension (HPH), wherein the protein expression of SphK1, but not SphK2, was significantly elevated in the lungs of mice and rats exposed to hypoxia (10% $O_2$) for 4 weeks (FIGS. 5C-5D, respectively). See Chen, et al. (2014) *Am. J. Resp. Crit. Care Med.* 190:1032-43.

Figure 6A:
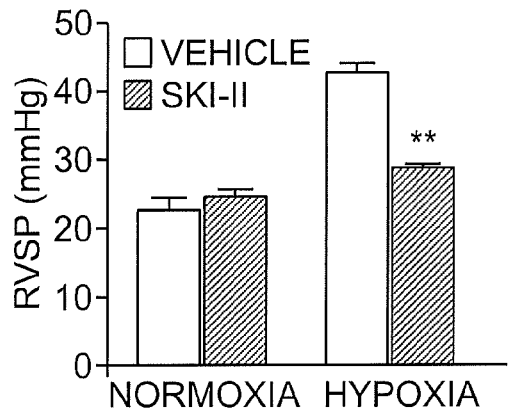
FIGS. 6A-6C show that SphK inhibition via SKI-II prevents hypoxia-mediated pulmonary hypertension in rats.
Figure 6B:
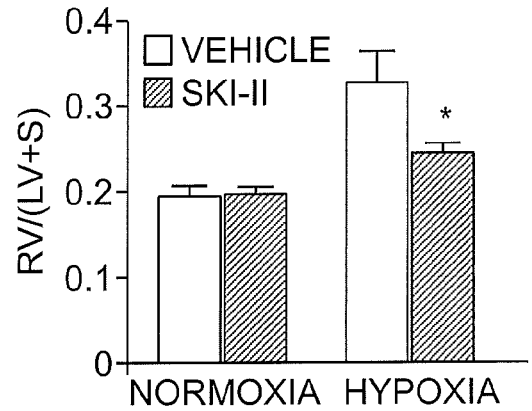
Figure 6C:
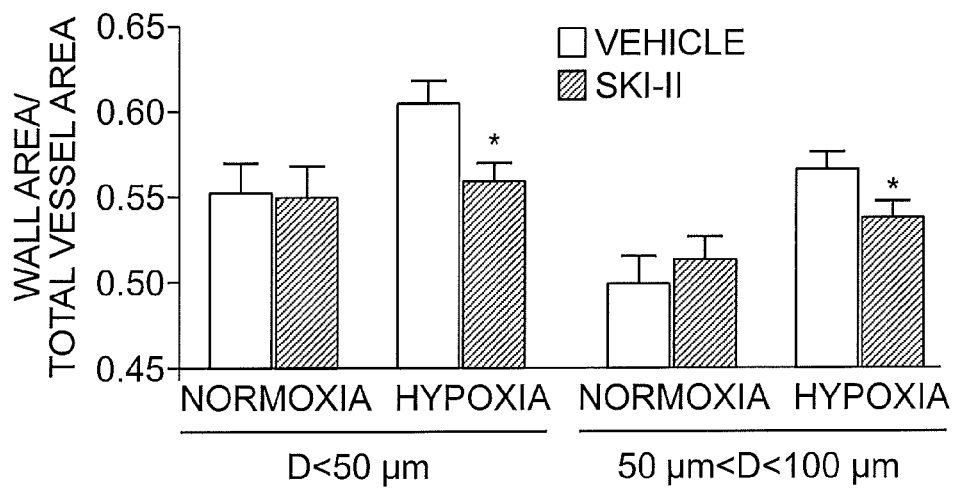

To further examine the role of SphKs in pulmonary hypertension, both SphK1 and SphK2 were inhibited in rats exposed to hypoxia using the non-selective inhibitor SKI-II. When compared with vehicle-treated rats, treatment with SKI-II (10 mg/kg body weight, intraperitoneally, once every other day for 3.5 weeks) prevented the development of HPH, as assessed by RVSP, RVH, and pulmonary vascular remodeling (FIGS. 6A-6C, respectively). See Chen, et al. (2014) *Am. J. Resp. Crit. Care Med.* 190:1032-43. Accordingly, selective inhibition of SphK1 is useful in the prevention and treatment of PAH.

EXAMPLE 7

Involvement of SphK1 in Chronic Obstructive Pulmonary Disease

It has been shown that alveolar macrophages from COPD patients are defective in their ability to phagocytose apoptotic cells despite smoking cessation (defective efferocytosis). In addition, it has been demonstrated that alveolar macrophages from COPD patients exhibit significantly higher mRNA-expression of both SphK1 and SphK2 (3.5- and 2.1-fold increase, respectively). Moreover, compared to non-smoking individuals, a significantly higher relative mRNA expression of SphK1 is found in current healthy smokers (6-fold increase) and current-smoker COPD patients (4.8-fold increase) compared to control subjects. See Barnawi, et al. (2015) *PLoS One* 10:e0122771. Accordingly, selective inhibition of SphK1 is useful in the prevention and treatment of COPD.

EXAMPLE 8

Involvement of SphK1 in Bronchopulmonary Dysplasia

Figure 7A:
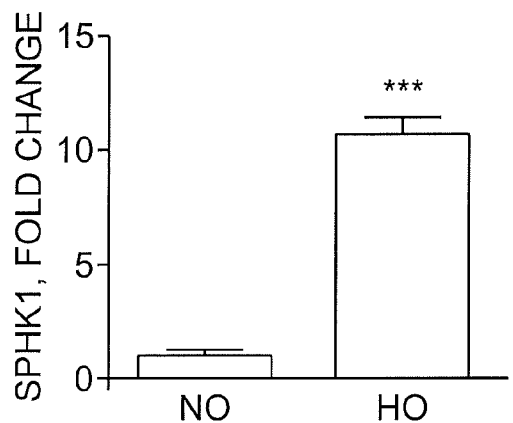
FIG. 7A-7D demonstrate the role of SphK1 in hyperoxia-induced bronchopulmonary dysplasia.
Figure 7B:
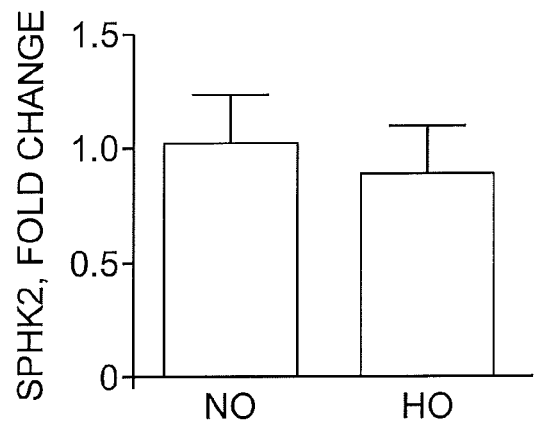
Figure 7C:
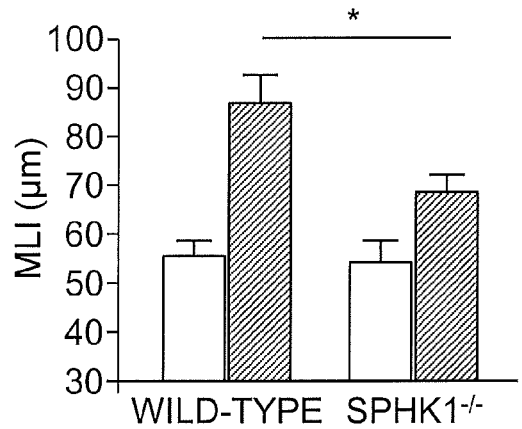
Figure 7D:
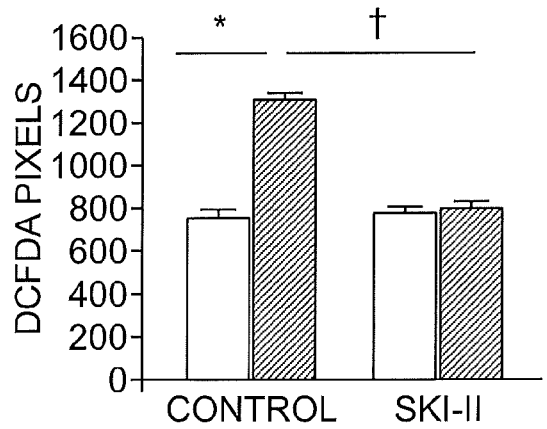

Bronchopulmonary dysplasia of the premature newborn is characterized by lung injury, resulting in alveolar simplification and reduced pulmonary function. It has been demonstrated that altered S1P signaling axis, in part, is responsible for neonatal lung injury leading to bronchopulmonary dysplasia. In particular, it has been shown that hyperoxia increases S1P levels and alters the expression SphK1, but not SphK2 (FIG. 7A-7B). In addition, when newborn wild-type, sphingosine kinase 1-deficient (Sphk1$^{-/-}$), sphingosine kinase 2-deficient (Sphk2$^{-/-}$), and S1P lyase-deficient (Sgpl1$^{+/-}$) mice were exposed to hyperoxia (75%) from postnatal day 1 to 7, Sphk1$^{-/-}$, but not Sphk2$^{-/-}$ or Sgpl1$^{+/-}$, mice offers protection against hyperoxia-induced lung injury, with improved alveolarization (FIG. 7C) and alveolar integrity compared with wild-type. Furthermore, SphK1 deficiency attenuates hyperoxia-induced accumulation of IL-6 in bronchoalveolar lavage fluids and NADPH oxidase (NOX) 2 and NOX4 protein expression in lung tissue. In vitro experiments using human lung microvascular endothelial cells show that exogenous S1P stimulates intracellular reactive oxygen species (ROS) generation, whereas SphK1 siRNA, or the SKI-II inhibitor against SphK1 (FIG. 7D), attenuates hyperoxia-induced S1P generation. Knockdown of NOX2 and NOX4, using specific siRNA, reduces both basal and S1P-induced ROS formation. See Harijith, et al. (2013) *Am. J. Pathol.* 183:1169-1182. Accordingly, selective inhibition of SphK1 is useful in the prevention and treatment of hyperoxia-induced lung injury, in particular bronchopulmonary dysplasia.

What is claimed is:

1. A method of treating a pulmonary disease or condition in a subject comprising administering to a subject in need of treatment an effective amount of a SphK1 inhibitor to treat the subject's pulmonary disease or condition, wherein the SphK1 inhibitor
    (a) exhibits at least a 20-fold greater selectivity for SphK1 than SphK2; and
    (b) is cell permeable, has an $IC_{50}$ value of less than 10 μM, or has a $K_i$ of less than 10 μM, or a combination thereof.

2. The method of claim 1, wherein the pulmonary disease or condition comprises pulmonary hypertension, adult respiratory distress syndrome, restrictive lung disease, chronic obstructive pulmonary disease, bronchiectasis, bronchiolectasis, bronchiolitis, bronchitis, emphysema, a diffuse interstitial or infiltrative lung disease, serofibrinous pleuritis, suppurative pleuritis, hemorrhagic pleuritis, a pleural effusion, idiopathic pulmonary fibrosis, bronchopulmonary dysplasia, hyperoxia or oxygen-induced lung injury, injury due to drug or chemotherapeutic toxicity, radiation-induced injury, or chemical injury.

3. The method of claim 1, wherein the SphK1 inhibitor comprises [(2R)-1-[[4-[[3-(benzenesulfonyl methyl)-5- methylphenoxy]methyl]phenyl] methyl] pyrrolidin-2-yl] methanol (PF-543) or a pharmaceutically acceptable salt thereof.

4. The method of claim 3, wherein the pharmaceutically acceptable salt is a citric acid salt.

5. The method of claim 1, wherein said SphK1 inhibitor is administered to the lungs of the subject.

6. A method of treating a pulmonary disease or condition in a subject comprising administering to a subject in need of treatment an effective amount of [(2R)-1-[[4-[[3-(benzenesulfonyl methyl)-5-methylphenoxy]methyl]phenyl]methyl] pyrrolidin-2-yl] methanol (PF-543), or a pharmaceutically acceptable salt thereof, to treat the subject's pulmonary disease or condition, wherein the pulmonary disease or condition comprises restrictive lung disease, bronchiectasis, bronchiolectasis, bronchitis, emphysema, a diffuse interstitial lung disease, a diffuse infiltrative lung disease, serofibrinous pleuritis, suppurative pleuritis, hemorrhagic pleuritis, idiopathic pulmonary fibrosis, bronchopulmonary dysplasia, hyperoxia or oxygen-induced lung injury, injury due to drug or chemotherapeutic toxicity, radiation-induced injury, or chemical injury.

7. The method of claim 6, wherein the pharmaceutically acceptable salt is a citric acid salt.

8. The method of claim 6, wherein said SphK1 inhibitor is administered to the lungs of the subject.

* * * * *